United States Patent [19]
Hagne et al.

[11] Patent Number: 5,567,156
[45] Date of Patent: Oct. 22, 1996

[54] INLAY, INLAY HOLDER, METHOD FOR TOOTH RESTORATION, AND TOOTH RESTORATION SET FOR CARRYING OUT THE METHOD

[75] Inventors: Leif Hagne, Skene; Rolf Greven, Ljungskile, both of Sweden

[73] Assignee: Nordiska Dental AB, Helsingborg, Sweden

[21] Appl. No.: 256,277

[22] PCT Filed: Jan. 4, 1993

[86] PCT No.: PCT/SE99/00002

§ 371 Date: Aug. 12, 1994

§ 102(e) Date: Aug. 12, 1994

[87] PCT Pub. No.: WO93/13726

PCT Pub. Date: Jul. 22, 1993

[30] Foreign Application Priority Data

Jan. 7, 1992 [SE] Sweden .................................. 9200020
Aug. 25, 1992 [SE] Sweden .................................. 9202428

[51] Int. Cl.[6] .............................. A61C 5/04; A61C 5/00
[52] U.S. Cl. ............................................ 433/226; 433/215
[58] Field of Search ............................. 433/215, 29, 226, 433/228.1

[56] References Cited

U.S. PATENT DOCUMENTS

| | | | |
|---|---|---|---|
| 4,234,310 | 11/1980 | Leuthard . | |
| 4,666,405 | 5/1987 | Ericson | 433/215 X |
| 4,666,406 | 5/1987 | Kanca, III | 433/215 X |
| 4,726,770 | 2/1988 | Kurer | 433/215 X |
| 4,971,558 | 11/1990 | Jacobi . | |
| 4,993,951 | 2/1991 | Schumacher . | |
| 5,017,140 | 5/1991 | Ascher | 433/215 |
| 5,030,093 | 7/1991 | Mitnick | 433/215 X |
| 5,272,184 | 12/1993 | Shoher et al. | 433/226 X |

FOREIGN PATENT DOCUMENTS

| | | |
|---|---|---|
| 8605085 | 9/1986 | WIPO . |
| 9209241 | 6/1992 | WIPO . |

*Primary Examiner*—Nicholas D. Lucchesi
*Attorney, Agent, or Firm*—Browdy and Neimark

[57] ABSTRACT

A prefabricated inlay (1) for restoring a tooth by application and fixation in a cavity prepared in the tooth and having essentially the same shape as the inlay part adapted for insertion, is provided with a pin (6) which projects from the inlay part not adapted for insertion and which is arranged to be received in an inlay holder. The whole inlay (1) is made of a material translucent to light that is suitable for curing a light-curing material used for fixing the inlay in the cavity. The inlay holder has a light source and a light guide having a tip (18) with a recess (19) for receiving the pin (6) of the inlay (1), such that the light generated by the light source can be guided through the light guide and the inlay (1) to the light-curing material. A tooth restoration set comprises a plurality of prefabricated frustoconical inlays (1), preferably having the same cone angle as well as several different narrow-end diameters, and a plurality of frustoconical burrs having the same cone angle as the inlays (1) as well as corresponding different narrow-end diameters.

9 Claims, 1 Drawing Sheet

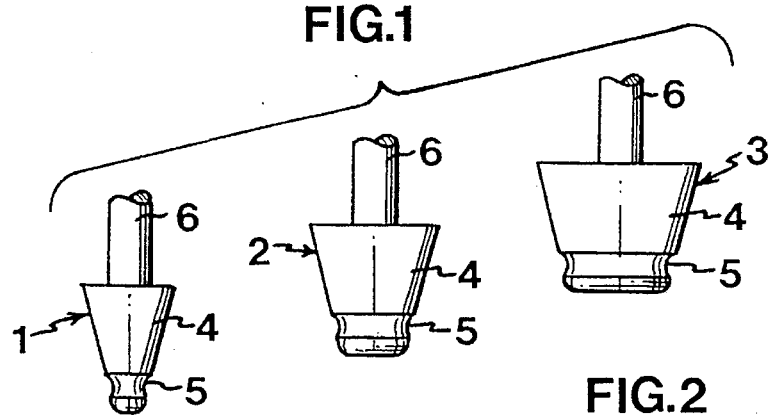
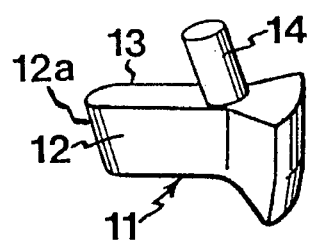
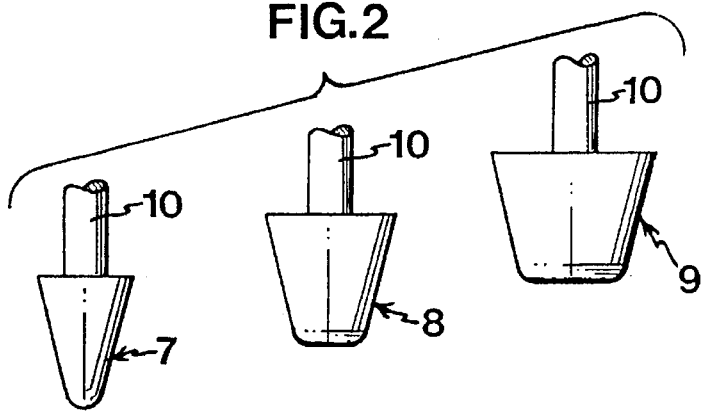
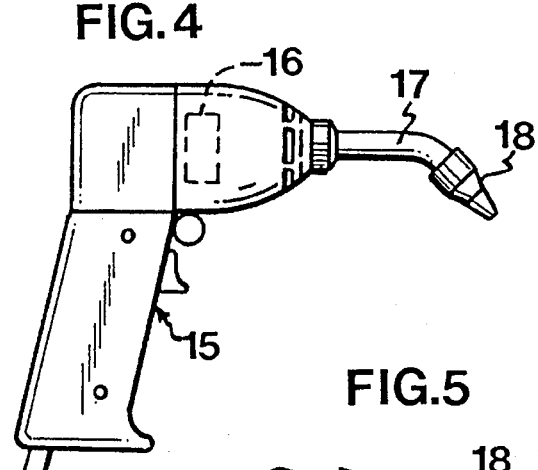
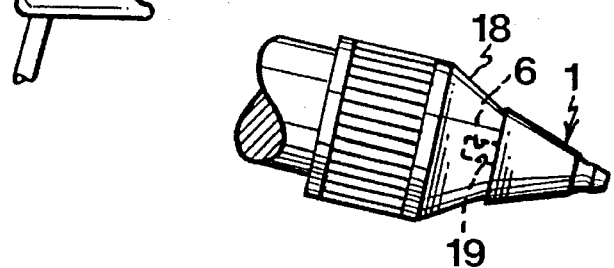
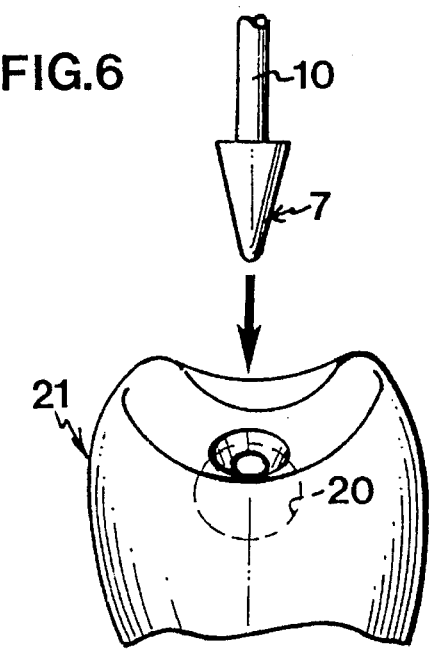

INLAY, INLAY HOLDER, METHOD FOR TOOTH RESTORATION, AND TOOTH RESTORATION SET FOR CARRYING OUT THE METHOD

BACKGROUND OF THE INVENTION

1. Technical Field of the Invention

Generally, the present invention relates to tooth restoration.

More precisely, the invention concerns a prefabricated inlay for restoring a tooth by application and fixation in a cavity prepared in the tooth and having essentially the same shape as the inlay part adapted for insertion.

The invention also bears upon an inlay holder for the application of a prefabricated inlay in a cavity prepared in a tooth and having essentially the same shape as the inlay part adapted for insertion.

The invention further encompasses a method for tooth restoration by applying and fixing a prefabricated inlay in a cavity prepared in the tooth and having essentially the same shape as the inlay part adapted for insertion.

Finally, the invention relates to a tooth restoration set for implementing the method.

2. Prior Art

Tooth restorations can be divided into indirect and direct restorations. In indirect restorations, an impression of a prepared cavity is made and employed for producing an inlay of e.g. porcelain or gold. Such restorations have, inter alia, the disadvantage of being time-consuming, and thus necessitate at least two visits to the dentist. Also, these restorations, which are fairly expensive, require the use of a temporary filling while the final inlay is being produced.

In direct restorations, use is commonly made of amalgam or composite materials. The composite materials have been developed to replace amalgam, but they are not suitable for large fillings, since they shrink when cured, have a relatively low abrasion resistance and strength, and involve the risk of gaps arising in the interface between the filling and the tooth.

Prefabricated inlays, preferably of ceramic material, have been developed as a further alternative to amalgam fillings. By using prefabricated inlays, a prepared cavity can be filled more or less completely with the inlay which is fixed therein, e.g. by a composite material. With this technique, the effect of the shrinkage of the composite material is considerably reduced. However, a certain risk of gap formation remains, unless the inlay covers the entire cavity opening. This also goes for the abrasion risk. Further, prior-art techniques for applying and fixing a prefabricated inlay in a cavity are imperfect, in that they do not enable accurate positioning and rapid fixation of the inlay in the cavity.

OBJECT AND SUMMARY OF THE INVENTION

The object of the present invention is, therefore, to provide an improved prefabricated inlay, as well as improved techniques for applying and fixing such an inlay in a prepared cavity.

According to the invention, this object is achieved by a prefabricated inlay which is of the type mentioned by way of introduction, and which is characterised in that it has a pin which projects from the inlay part not adapted for insertion and which is arranged to be received in an inlay holder, and that the whole inlay is made of a material translucent to light that is suitable for curing a light-curing material used for fixing the inlay in the cavity. Since the pin can be received in an inlay holder, it is possible to have total control of the positioning of the inlay in the cavity. Owing to the fact that the inlay is made of the above translucent material and the fact that a light-curing material is used for fixing the inlay in the cavity, fixation can be rapidly performed by guiding light via the inlay to the surrounding fixation material in the cavity.

To achieve perfect control of the positioning of the inlay when inserted in the cavity, the pin conveniently has a round cross-sectional shape to be received in an optional rotational position in a corresponding recess in the inlay holder.

For cavities that can be given a circular opening, the inlay according to the invention is conical and has the same cone angle as a burr used for preparing the cavity opening. Thus, the inlay can be made to completely fill at least the cavity opening, thereby eliminating the risk of gap formation. The material of the inlay then determines abrasion resistance.

For cavities having a non-round opening, part of the opening may be round, in which case use is advantageously made of an at least partly conical inlay with the same cone angle as a conical burr used for preparing the cavity opening.

Advantageously, the inlay is made of a ceramic or glass-ceramic material, suitably one that can be cast. When a conical inlay cannot be used, prefabricated inlays of other shapes, preferably a partly conical shape, may of course be used.

The prefabricated inlays primarily serve to replace missing dental enamel in the cavity, but they may also replace dentine to some extent.

The conical inlay, as well as the corresponding burr, preferably has the shape of a truncated cone. The inlay may, preferably closest to the narrow end, be provided with one or more raised portions and/or depressions serving to improve mechanical retention.

According to the invention, an inlay holder of the type mentioned by way of introduction has a light source for generating light suitable for curing a light-curing material for fixing the inlay in the cavity, and a light guide receiving the light from the light source and having a tip with a recess adapted to receive a pin which projects away from the inlay part adapted for insertion, such that the light generated by the light source can be guided through the light guide and the inlay to the light-curing material. The inventive inlay holder enables secure positioning of the inlay in the cavity. Since the inlay holder is integrated with the light guide for the curing light, extremely rapid fixation of the inlay in the cavity can be attained. Among other things, this is necessary in order to prevent the formation of gaps at the interfaces between the fixation material and, respectively, the inlay and the tooth. The inlay holder may easily be produced by modifying a conventional curing lamp.

The rotational position of the inlay in relation to the inlay holder can be varied by giving the recess in the light-guide tip a round cross-sectional shape. Then, the pin of the inlay should have the same round cross-sectional shape.

In a preferred embodiment, the light source of the inlay holder generates blue light in the wave range of 400–500 nm. The light source may be a halogen light source or a laser light source.

According to the invention, the method for restoration mentioned by way of introduction is characterised by preparing at least a portion of the cavity opening by means of a conical burr so as to impart an at least partly conical shape to this portion; and applying and fixing in the cavity an inlay which has a part corresponding to said portion and having exactly the same cone angle as the conical burr. With this method, the cavity opening will be completely filled with the conical inlay, especially when entirely conical. The risk of shrinkage and gap formation is thus almost completely eliminated.

In a preferred mode of operation, a pin projecting from the thick end of the inlay is inserted in a corresponding recess in an inlay holder; the inlay is fixed in the cavity by means of a light-curing material; and light for curing this material is guided through the inlay holder and the inlay. It is to be understood that the inventive method enables very accurate positioning and extremely rapid fixation of the inlay in the cavity.

Conveniently, the preferably pre-etched inlay is silanised prior to application in the cavity.

According to the invention, a tooth restoration set for implementing the above method is characterised by a plurality of prefabricated frustoconical inlays, preferably having the same cone angle as well as several different narrow-end diameters, and a plurality of frustoconical burrs having the same cone angle as the inlays as well as corresponding different narrow-end diameters. Preferably, the number of burrs in the set is smaller than the number of conical inlays but yet sufficient for a burr of each type always to be available, regardless of the sterilisation of used burrs required.

Preferably, each inlay in the set has a pin which projects from the thick end and is adapted to be received in an inlay holder provided with a recess designed to receive the pin.

To enable contactless handling, the inlays are suitably fixed in a container in such a position that they can be removed therefrom by means of the inlay holder alone.

Preferably, the burrs are diamond burrs which are diamond-coated also on the end surface of the narrow end. Further, the inlays are preferably translucent to light that is suitable for curing a light-curing material used for fixing an inlay in a tooth cavity.

It will be appreciated that the present invention encompassing the prefabricated inlay, the inlay holder, the restoration method and the restoration set involves considerable improvements in direct tooth restorations. Thus, the invention enables tooth restoration to be performed in a very short time. Further, the restoration according to the invention is of high quality as to appearance as well as durability. As a result of the short time required and the materials used, the costs for performing a tooth restoration with the aid of the invention can be kept quite low.

The fact that the cavity should have essentially the same shape as the inlay part adapted for insertion is to be understood to mean that at least the opening part of the cavity and the corresponding inlay part should have a substantially mating shape.

BRIEF DESCRIPTION OF THE DRAWINGS

The invention will be described in more detail below with reference to the accompanying drawing, in which FIG. 1 is a side view of three prefabricated inlays according to the invention;

FIG. 2 is a side view of three corresponding burrs according to the invention used for preparing a cavity for inlays of the type shown in FIG. 1;

FIG. 3 is a perspective view of another embodiment of an inlay according to the invention;

FIG. 4 is a side view of an inlay holder according to the invention;

FIG. 5 is a detail view of a light-guide tip of the inlay holder in FIG. 4; and

FIG. 6 is a perspective view illustrating the method according to the invention.

FIG. 1 shows prefabricated, inventive inlays 1–3 which are made of a ceramic or glass-ceramic material whose properties are as similar to those of dental enamel as possible. This material should preferably be castable or industrially sintered, so that the inlays 1–3 may easily be produced in large series of high dimensional accuracy. The inlays 1–3 have a frustoconical part 4 having a circular cross-section and being adapted for insertion into a cavity in a tooth. At the narrow end of the frustoconical part 4, the inlays 1–3 have a recess in the form of a circumferential groove 5 serving to improve the mechanical retention of the inlay when this has been applied in the tooth cavity. Alternatively, the inlays 1–3 may, for the same purpose, be provided with raised portions which, however, must not project radially to such an extent that the inlays 1–3 cannot be inserted in the cavity at issue. Neither the depressions nor the raised portions are compulsory, since the retention needed can often be achieved all the same, especially if the inlays are etched. The thick end of the conical inlays 1–3, i.e. the inlay part not adapted for insertion, has an axially projecting pin 6 of preferably round cross-section.

The narrow end of the conical part 4 preferably has a rounded shape.

In a preferred embodiment, the cone angle of the frustoconical part 4 is approximately 28°. Naturally, the invention is not restricted to this angle, but encompasses other cone angles as well. In different embodiments, the inlays 1–3 can have different diameters at the narrow end but essentially the same height at the frustoconical part 4, as illustrated in FIG. 1.

FIG. 2 is a side view of three different, frustoconical burrs 7–9. Preferably, the burrs 7–9 have a diamond coating both on the circumferential surface of the frustoconical part and on the end surface of the narrow end. To enable mounting in conventional drilling equipment, the burrs 7–9 have a shank 10 projecting axially from the thick end. According to the invention, the cone angle of the burrs 7–9 should be identical with that of the corresponding inlays 1–3 that are to be applied in cavities prepared by the burrs.

FIG. 3 shows another embodiment of an inlay 11 according to the invention. This inlay 11 is substantially L-shaped and has, in accordance with the invention, two lateral surfaces 12, 13, which either are parallel or converge slightly downwards, on one branch of the L. This branch, which is to be contained in the occlusal part of the cavity, has, in accordance with the invention, a conical end 12a, i.e. a partly conical portion. Alternatively, the end 12a may be partly cylindrical and be inclined obliquely inwards-downwards. The inlay 11 is intended to for making a "class II" filling, in which case the above branch is to be accommodated in an occlusal part of the cavity, while the other branch of the L is to be accommodated in a proximal part of the cavity. A pin 14 projects upwards from the future outer part of the occlusal surface of the inlay 11 at an acute angle to the branch with the lateral surfaces 12, 13. Conveniently, the pin 14 has the same shape as the pin 6 in FIG. 1, and the inlay 11 is made of the same material as the inlays 1–3 in FIG. 1. By angling the pin 14, the inlay 11 may, when applied, be simply pressed against both the occlusal opening edges of the cavity and the adjoining tooth, thereby optimising positioning of the inlay 11 in the cavity, by the forces that act on the inlay 11 after restoration being directly transferred to the underlying original tooth material. By the special design of the end 12a, the inlay can, when applied, be axially displaced, and consequently in mesiodistal direction, to optimise positioning in the cavity.

The embodiment of an inlay holder according to the invention shown in FIG. 4 consists of a conventional curing lamp 15 containing a light source 16, e.g. a halogen or laser light source, for generating light suitable for curing a light-curing material in order to fix e.g. the inlay 1 in a cavity prepared therefor. Further, the curing lamp 15 has a light guide 17 extending from the light source 16 out into a tip 18. As illustrated in more detail in FIG. 5, a recess or hole 19 is, in accordance with the invention, provided in the free end of the light-guide tip 18 and has a cross-sectional shape corresponding to that of the pins 6, 14. This recess may be slightly conical, so that, after e.g. the pin 6 has been inserted therein, e.g. the inlay 1 is retained in a fixed position in the light-guide tip 18, there being good transmission from the light-guide tip 18 of the light generated by the light source 16 into the pin 6 and through the whole inlay 1.

The method according to the invention will now be described with reference to FIG. 6, involving the use of an inlay 1 of the type shown in FIG. 1 for the restoration of an occlusal cavity 20 in a tooth 21. In a first step, the cavity 20 is prepared by drilling its interior to a sufficient extent. Then, the opening of the cavity 20 is prepared by means of a burr of the type shown in FIG. 2. These steps may also be performed in the reverse order. Then, the internal surface of the cavity is insulated by a suitable insulating material, e.g. a glass ionomer. If a non-conical inlay, e.g. an inlay of the type shown in FIG. 3, is to be employed, a gauge can be used for determining the size and the shape of the inlay. In the case described, use is made of a conical inlay 1 with a size corresponding to the burr used. Preferably, this inlay is pre-etched, and is cleaned, dried and silanised after being fixed in the inlay holder. Prior to the application of the inlay 1 in the cavity 20, the latter may be etched with phosphoric acid and, after drying, be filled with a fixing material, e.g. a light-curing composite material. Preferably, use is made of a dual composite which is not only slowly chemically curing but also rapidly light-curing. Immediately before application of the inlay 1 in the cavity, the inlay part adapted for insertion can be wetted with a resin. Then, the inlay 1 is pressed down into the cavity 20 until its circumferential surface makes firm contact with the opening of the cavity 20, whereupon the light source 16 of the inlay holder 15 is lit for rapid curing of the composite material, thereby fixing the inlay 1 in the cavity 20. The inlay holder 15 may then be removed by pulling the tip 18 off the pin 6. Alternatively, the pin 6 can be broken by means of the inlay holder 15. Finally, restoration is completed by grinding and polishing the exposed part of the inlay 1 to the desired shape and finish.

It goes without saying that several modifications of the embodiments described above are conceivable within the scope of the invention as defined in the appended claims.

We claim:

1. A method for restoring a tooth by applying and fixing a prefabricated inlay (1; 11) in a cavity (20) prepared in the tooth and having essentially the same shape as the inlay adapted for insertion, comprising the steps of preparing at least a portion of the cavity by means of a conical burr (7–9) so as to impart an at least partly conical shape to said portion; and applying and fixing in the cavity an inlay (1; 11) which has a part corresponding to said portion and having the same cone angle as the conical burr.

2. A method as claimed in claim 1 including the steps of making the opening of the cavity (20) entirely conical; and applying and fixing a conical inlay (1) in the cavity.

3. A method as claimed in claim 1, wherein said inlay further comprises a pin and including the steps of inserting said pin (6), which projects away from a thick end of the inlay (1), into an inlay holder (15) having a corresponding recess (19); fixing the inlay in the cavity (20) by means of a light-curing material; and guiding light for the curing of said material through the inlay holder (15) and the inlay (1).

4. A method as claimed in claim 1, wherein said inlay is pre-etched including the step of silanising said pre-etched inlay (1) prior to application.

5. A tooth restoration set, comprising a plurality of prefabricated frustoconical inlays (1), each having the same cone angle as well as a different diameter at a narrow-end, and a plurality of frustoconical burrs (7–9) having the same cone angle as the inlays (1) as well as corresponding different diameter at a narrow-end.

6. A set as claimed in claim 5, wherein each inlay (1) has a pin (6) which projects away from a thick end and is receivable in an inlay holder.

7. A set as claimed in claim 5, wherein the inlays (1) are fixed in a container in such a position that they can be removed from the container by means of an inlay holder (15) alone.

8. A set as claimed in claim 5, wherein the burrs (7–9) are diamond burrs which are each diamond-coated on an end surface of the narrow end.

9. A set as claimed in claim 5, wherein the inlays (1) are translucent to a light that is suitable for curing a light-curing material used to fix an inlay in a tooth cavity.

* * * * *